United States Patent [19]

Schmitz

[11] Patent Number: 5,167,641
[45] Date of Patent: Dec. 1, 1992

[54] AUTO-RETRACTING NEEDLE INJECTOR SYSTEM

[75] Inventor: William L. Schmitz, Hemet, Calif.

[73] Assignee: Arnis, Inc., Murrieta, Calif.

[21] Appl. No.: 706,947

[22] Filed: May 29, 1991

[51] Int. Cl.⁵ ............................................ A61M 5/32
[52] U.S. Cl. .................... 604/196; 604/110; 604/187; 604/232; 604/403; 604/201
[58] Field of Search ........ 604/134, 187, 110, 194–198, 604/200, 201, 218, 232, 239, 403, 415, 135; 128/919

[56] References Cited

U.S. PATENT DOCUMENTS

| | | |
|---|---|---|
| 3,064,650 | 11/1962 | Lewis . |
| 3,072,608 | 11/1972 | Tibbs . |
| 3,494,358 | 2/1970 | Fehlis et al. . |
| 3,712,301 | 1/1973 | Sarnoff . |
| 3,797,489 | 3/1974 | Sarnoff . |
| 3,880,163 | 4/1975 | Ritterskamp . |
| 3,882,863 | 5/1975 | Sarnoff et al. . |
| 4,194,505 | 3/1980 | Schmitz . |
| 4,316,463 | 2/1982 | Schmitz . |
| 4,333,457 | 6/1982 | Margulies .................. 604/232 X |
| 4,413,991 | 11/1983 | Schmitz . |
| 4,552,559 | 11/1985 | Donaldson et al. .......... 604/198 |
| 4,553,962 | 11/1985 | Brunet ........................ 604/198 |
| 4,666,436 | 5/1987 | McDonald et al. .......... 604/198 |
| 4,767,413 | 8/1988 | Haber et al. ................ 604/198 |
| 4,902,279 | 2/1990 | Schmitz et al. . |
| 4,936,830 | 6/1990 | Verlier ........................ 604/110 |
| 4,941,883 | 7/1990 | Venturini .................... 604/186 |
| 4,990,135 | 2/1991 | Truesdale ................... 604/47 |
| 5,007,903 | 4/1991 | Ellard ........................ 604/195 |
| 5,046,508 | 9/1991 | Weissler ..................... 128/763 |
| 5,092,843 | 3/1992 | Monroe et al. ............. 604/138 |
| 5,092,853 | 3/1992 | Couvertier ................. 604/195 |
| 5,098,382 | 3/1992 | Haber et al. ............... 604/110 |

FOREIGN PATENT DOCUMENTS

| | | | |
|---|---|---|---|
| 0593226 | 2/1960 | Canada ...................... | 604/195 |
| 0933478 | 9/1955 | Fed. Rep. of Germany .. | 604/232 |
| 2506161 | 11/1982 | France ....................... | 604/187 |
| 0933976 | 8/1963 | United Kingdom .......... | 604/200 |
| 1008915 | 11/1965 | United Kingdom .......... | 604/200 |
| 9006148 | 6/1990 | World Int. Prop. O. ...... | 604/110 |

OTHER PUBLICATIONS

Autoject Preliminary Operating Instructions; Own Mumford Limited; no date.
Schmitz et al.—Unpublished drawings of prototype injector; no date.
Insulin Therapy at Its Simplest advertisement; Squibb-Novo, Inc.; Jul. 1988.
"Introducing Ject Aid TM Automatic Insulin Injector" brochure; Autoject Systems Inc., Hemet, Calif.; 1 p.; no date.

Primary Examiner—C. Fred Rosenbaum
Assistant Examiner—Mark O. Polutta
Attorney, Agent, or Firm—John Connors

[57] ABSTRACT

A medical injector system includes a hypodermic ampule having a body, a piston sealingly forwardly movable therein for defining a medicament chamber, a pierceable seal closing a front extremity of the ampule, a needle movably axially supported by the piston and biased rearwardly toward a retracted, cocked position. An actuator removably receives the ampule, and has a spring-loaded plunger for advancing the needle, and then the piston, whereby the needle reaches an extended position, medicament being injected from the needle during the forward movement of the piston. When the plunger is released, it retracts from the needle and the piston, the needle automatically retracting into the ampule for preventing accidental injury and contamination that might otherwise result from having the used needle in an exposed position.

13 Claims, 1 Drawing Sheet

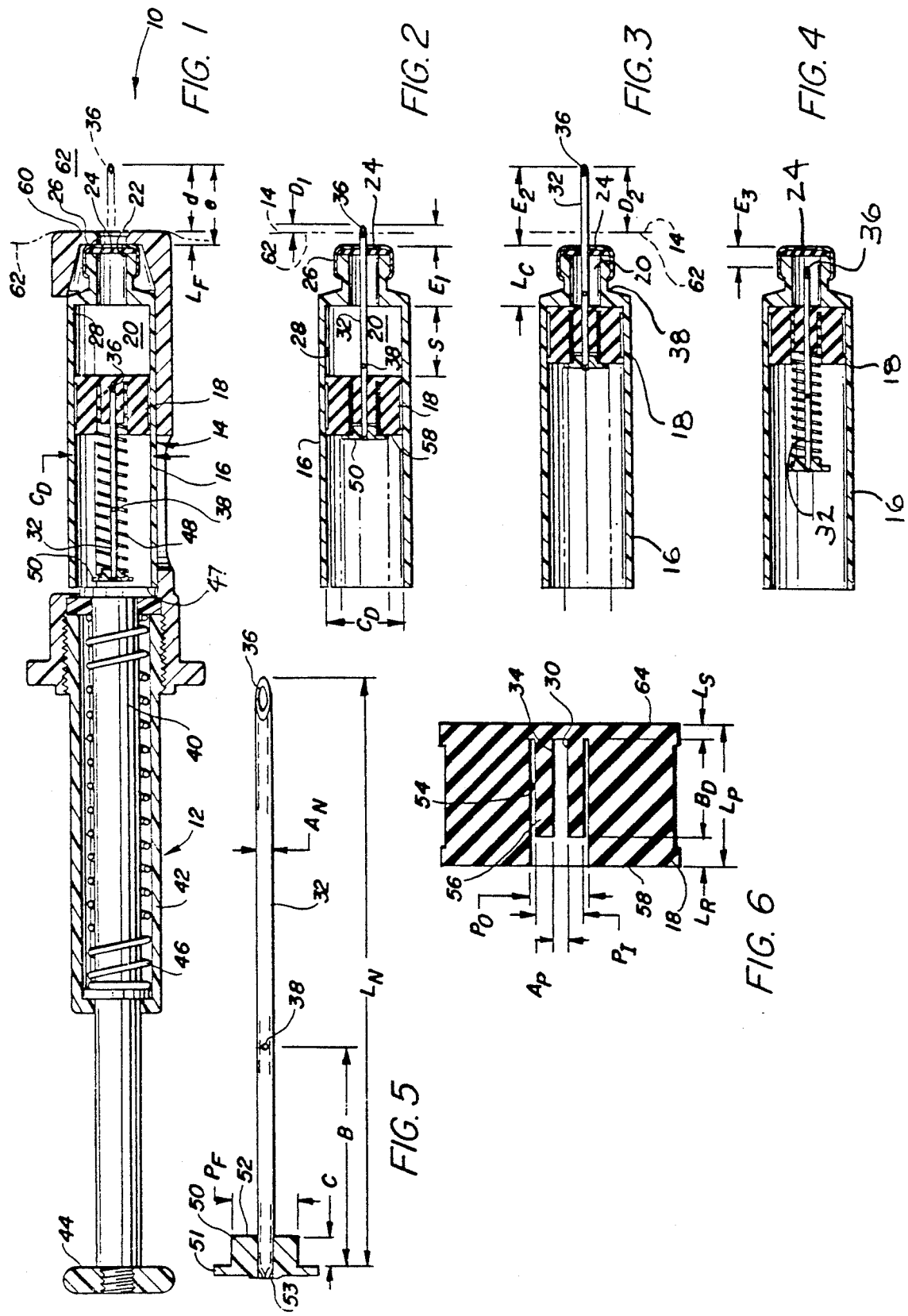

AUTO-RETRACTING NEEDLE INJECTOR SYSTEM

BACKGROUND

The present invention is related to hypodermic syringes and ampules, and mechanisms for causing needles thereof to penetrate the flesh for delivery of medicaments therefrom into the flesh. While the invention is useful to physicians, paramedics, nurses or the like, and to patients who are required to self-administer medicaments such as insulin in cases of diabetes.

Injector devices for facilitating hypodermic injections are known, both for medicament ampules that are furnished with the injector device, and for conventional hypodermic syringes that are operated by the device. In the case of injection from self-contained ampules, see, for example, U.S. Pat. Nos. 4,194,505, 4,316,463, and 4,413,991 to the present inventor, and U.S. Pat. No. 3,712,301 to Sarnoff. For injection from conventional syringes, see U.S. Pat. Nos. 4,494,358 to Fehlis, 3,702,608 to Tibbs, and 3,880,163 to Ritterskamp, as well as the first above-identified patent.

It is also known to provide a "tracked" injection wherein the medicament is caused to issue from the needle during movement of the needle into the patient's flesh for preventing tissue damage that would otherwise be caused by a "balloon" injection, wherein substantially all of the medicament is deposited after the needle reaches maximum penetration.

A problem with the syringe and ampule devices of the prior art is the danger of injury to the patient and others by the needle subsequent to the delivery of the medicament. (In the case of syringes, such danger is also present prior to medicament delivery.) For example, medical care providers can be accidentally scratched or punctured by the needle, being potentially harmed aside from the injury itself by residual quantities of the medicament. This danger is a particularly serious in situations wherein the needle may have become contaminated by dangerous substances, such as body fluids containing HIV virus.

Thus there is a need for a hypodermic injector device that reliably and safely facilitates administration of a medicament dosage without subjecting the patient or others to contamination or injury from the device, that is effective for delivery of the medicament in a tracked injection below a predetermined depth, and that is inexpensive to provide and easy to use.

SUMMARY

The present invention is directed to a safety injector system that meets this need. The system includes an ampule having a housing that forms a portion of a medicament chamber and has a front opening in fluid communication with the chamber, a resilient closure member for sealingly closing the front opening, a resilient seal means for sealingly closing a rear portion of the chamber; a tubular tissue-piercing needle movably supported within the housing for movement from a cocked position to an extended position, the needle having a front outlet and an inlet rearwardly located relative to and in fluid communication with the outlet, and needle biasing means for biasing the needle rearwardly from the extending position; actuation means for advancing the needle from the cocked position to the extended position in response to external force and compressing the chamber for feeding the medicament from the chamber into the inlet and out of the outlet of the needle; and means for permitting movement of the needle by the needle biasing means from the extended position to a final position in response to removal of the external force such that the outlet of the needle is enclosed within the chamber in the final position for preventing accidental contact with the needle subsequent to use of the system.

The actuation means can include a piston sealingly axially movable in the housing, the seal means being located on the piston. A needle guide passage can be carried by the piston, the seal means forming a pierceable end termination of the needle guide passage. Preferably the needle biasing means can include a first helical compression spring coupled between the needle and the piston for urging the needle rearwardly relative to the piston. A flange member can be rigidly connected proximate a rear extremity of the needle for receiving a rear extremity of the first spring, the needle guide passage extending within a front extremity of the first spring. The flange member preferably contacts the piston for limiting forward movement of the needle. A pierceable cover member can sealingly close a rear portion of the housing, the piston and the needle being sealingly enclosed between the cover member and the closure member when the needle is in the cocked position, the cover member being pierced by application of the external force.

The actuation means can include means for coupling the inlet of the needle to the chamber between an intermediate position and the extended position of the needle, and means for feeding a major portion of the medicament from the outlet during movement of the needle between the intermediate and extended positions. The needle can be slidably supported on a piston sealingly slidably supported by the housing for sizing the chamber, the seal means being located on the piston proximate the needle outlet when the needle is in the cocked position. The actuation means preferably includes needle limit means for limiting forward movement of the needle relative to the piston between the intermediate and extended positions, the piston being moved forwardly by the needle limit means during the feeding of the medicament.

The system can also include an actuator unit for operating the ampule, including a frame for releasably receiving the ampule; a plunger axially movable in the frame and having a handle portion extending rearwardly therefrom; and a plunger spring connected between the frame and the plunger for rearwardly biasing the plunger, the needle being advanced from the cocked position to the extended position in response to a forwardly directed external force on the handle portion, the chamber being compressed by forward movement of the piston for feeding the medicament from the chamber, into the inlet and out of the outlet of the needle, the plunger retracting from the ampule when the external force is removed.

DRAWINGS

These and other features, aspects, and advantages of the present invention will become better understood with reference to the following description, appended claims, and accompanying drawings where:

FIG. 1 is a fragmentary sectional elevational view of a safety medicament injector system according to the present invention, the system including a medicament ampule, the ampule being in a cocked configuration;

FIG. 2 is a sectional elevational detail view showing the ampule of the system of FIG. 1 in an intermediate configuration;

FIG. 3 is a detail view as in FIG. 2, showing the ampule in an extended configuration;

FIG. 4 is a detail view as in FIG. 2, showing the ampule in a final retracted configuration;

FIG. 5 is a fragmentary longitudinal sectional view of a needle portion of the ampule of FIG. 1;

FIG. 6 is a longitudinal sectional view of a piston of the ampule of FIG. 1.

DESCRIPTION

The present invention is directed to a hypodermic injector system for safely administering a medicament to a patient without hazardous exposure of the patient or medical providers to contamination or injury following use of the system. With reference to FIGS. 1-6 of the drawings, an injector system 10 according to the present invention includes an actuator 12 and a disposable ampule 14 removably received therein, the ampule 14 having a housing or body 16 and a piston 18 sealingly axially movable therein for defining a variable volume chamber 20. A front opening 22 of the body 16 is sealingly closed by a resilient disk-shaped closure member 24, the closure member 24 being retained on the body 16 by a crimped band in a conventional manner.

The piston 18 is formed of a suitable elastomer for sealing contact with a bore 28 of the body 16, and having a passage 30 formed therein for guiding a tubular needle 32 that is carried by the piston 18, the passage 30 being separated from the chamber 20 by a seal portion 34 of the piston 18, the needle 32 being sharpened at a forward end outlet 36 thereof for piercing the seal portion 34 and the closure member 24 as described below, the outlet 36 being located proximate the seal portion 34 in a cocked position of the needle 32 as shown in FIG. 1. The needle 32 has a side inlet 38 formed therein, the inlet 38 being in fluid communication with the outlet 36 for delivery of the medicament from the chamber 20 when the inlet 38 is within the chamber 20 as shown in FIGS. 2 and 3.

The needle 32 is advanced from the cocked position of FIG. 1 to an extended position (shown in FIG. 3) by a plunger 40 of the actuator 12, the plunger 40 being axially slidably supported in a frame 42 of the actuator 12 and having a handle 44 fixably connected at a rear extremity thereof for receiving an external actuating force from an operator of the system 10, the plunger 40 being biasingly connected to the frame 42 by a helical compression plunger spring 46 for moving rearwardly from the needle 32 upon removal of the external force. A pierceable cover member 47 sealingly closes the rear of the body 16 for sealingly enclosing the needle 32 within the ampule 14. The plunger 40 pierces the cover member 47 as it moves toward the needle 32 upon application of the external actuating force.

An important feature of the present invention is that the needle 32 is biased rearwardly for retraction into the body 16 when the plunger moves rearwardly from the needle 32. For this purpose, a helical compression needle spring 48 is interposed between the piston 18 and a flange member 50 that is rigidly connected to the rear extremity of the needle 32, the flange member 50 having an outer flange portion 51, and a body portion 52 that extends into a rear extremity of the needle spring 48 for locating same. The piston 18 has a cylindrical spring cavity 54 formed therein for receiving a front portion of the needle spring 48, the passage 30 being formed within a boss portion 56 of the piston 18, the boss portion 56 being concentrically spaced within the spring cavity 54 and terminating forwardly of a rear face 58 of the piston 18 for clearing the body portion 52 of the flange member 50 when the flange member 50 contacts the rear face 58 as shown in FIGS. 2 and 3. The rear extremity of the needle 32 is sealingly crimped closed as indicated at 53 in FIG. 5, the crimped portion 53 also serving to anchor the flange member 50 on the needle 32.

As shown in FIG. 1, the ampule 14 is retained axially behind a flange portion 60 of the frame 42 of the actuator 12, the flange portion 60 having an axial flange length $L_F$. The needle 32 projects by a variable extension distance e forwardly of the ampule 14 in response to operation of the plunger 40, and by a corresponding penetration depth d from the flange portion 60 into an injection site 62 of the patient. As further shown in FIG. 2, the needle extends forwardly of the ampule 14 by a first or initial extension distance $E_1$ (and into the injection site 62 by a corresponding initial depth $D_1$) when the flange member 50 initially contacts the rear face 58 of the piston 18, the piston 18 being movable forwardly from its initial position by a stroke S in sliding engagement with the bore 28 of the body 16, the bore 28 having a chamber diameter $C_D$. As shown in FIG. 3, when the piston 18 is moved fully forward within the bore 28, being located behind the front of the ampule 14 by an axial front cylinder length $L_C$, the needle 32 extends forwardly of the ampule 14 by a second extension distance $E_2$ (and into the injection site 62 by a corresponding full depth $D_2$). Following removal of the external force as described above, the needle 32 is retracted by the needle spring 48 to a distance $E_3$ within the ampule 14 as shown in FIG. 4.

As shown in FIG. 6, the piston 18 has an overall piston length $L_P$ between a front face 64 and the rear face 58, the seal portion 34 being flush with the front face 64 and having a wall thickness or seal length $L_S$, the spring cavity 54 also extending to the same distance from the front face 64. The spring cavity 54 is formed with a cavity outside diameter $P_O$ and a cavity inside diameter $P_I$ for clearing the needle spring 48, the passage 30 within the boss portion 56 having a passage diameter $A_P$, the boss portion 56 extending to a boss depth $B_D$ from the rear face 58 of the piston 18. As shown in FIG. 5, the needle 32 has an outside diameter $A_N$, extending forwardly by a needle length $L_N$ from the front of the flange portion 51 forwardly to the end outlet 36, the body portion 52 extending forwardly of the flange portion 51 by a body distance C and having a flange body diameter $P_F$. The side inlet 38 of the needle 32 is located forwardly of the flange portion 51 by an inlet distance B.

According to the present invention, the inlet distance B is slightly greater than the piston length $L_P$ for excluding the medicament from the needle 32 until the flange member 52 is nearly seated against the rear face 58 of the piston 18. Also, the distance $L_R$ is slightly greater than the body distance C for permitting the flange portion 51 to seat against the rear face 51. Thus the initial extension distance $E_1$ in FIG. 2 is equal to the needle length $L_N$ less the total of the piston length $L_P$, the flange length $L_C$, and the stroke S. Correspondingly, the initial penetration depth $D_1$ is the first extension distance $E_1$ reduced by the flange length $L_F$ of the flange portion 60. Similarly, the full extension distance $E_2$ of FIG. 3 is equal to the length $L_N$ reduced by the piston length $L_P$ and the distance $L_C$, the corresponding full penetration depth $D_2$ being the full extension distance $E_2$ reduced by the flange length $L_F$.

Preferably, the initial penetration depth $D_1$ is approximately 0.09 inch for avoiding loss of the medicament from the injection site 62. Also, a conveniently configured combination of the body 16, the closure member 24 and the band 26 has the distance $L_C$ being approximately 0.3 inch. For operation with the chamber diameter $C_D$ in the range of between approximately 0.25 inch to approximately 0.5 inch, the length $L_P$ of the piston 18 can be approximately 0.385 inch, which is sufficient for accommodating the needle spring 48 in its compressed condition as described below.

A preferred configuration of the needle 32 and the flange member 50 has the needle length $L_N$ being approximately 1.2 inches, the inlet distance B being approximately 0.45 inch for use with the body 16 and the piston 18 configured as described above.

The tracked injection feature of the present invention is obtained by entry of the side inlet 38 of the needle 32 into the chamber 20, ahead of the piston 18 as shown in FIG. 2, before the needle 32 reaches the extended position of FIG. 3, whereby the medicament flows from the chamber, through the needle 32, and into the flesh at the injection site 62 during forward movement of the piston 18.

In a preferred exemplary embodiment of the present invention providing a volumetric medicament capacity of $\frac{1}{2}$ cc of the ampule 14, the chamber diameter $C_D$ is about 0.4 inch in diameter, the stroke S of the piston 18 being about 0.39 inch.

The present invention provides a safe and convenient solution to the problem of administering injections by those not having specialized medical training. The system 10 can easily be operated by the person receiving the injection, and the targeted injection site 62 does not need to be in view. Moreover, the injection is quick and painless. Most importantly, the needle 32 retracts automatically into the ampule 14 upon release of the plunger 40, thereby avoiding the special hazards associated with accidental exposure to the needle 32 subsequent to operation of the system 10.

The springs 46 and 48 are fabricated from a suitable spring-tempered material such as corrosion-resistant steel. In a preferred configuration of the ampule 14, the needle spring 48 is formed of 0.020 inch diameter steel as described above, having 15 turns at approximately 12.6 turns per inch on an approximately 0.230 inch pitch diameter. The needle spring 48 has a free length of approximately 1.19 inch, and a solid length approximately 0.30 inch, opposite ends of the spring 48 being close-wound. Sufficient clearance for the spring 48 within the piston 18 is obtained with the cavity outside diameter $P_O$ of the spring cavity 54 being approximately 0.256 inch, the cavity inside diameter $P_I$ being approximately 0.204 inch. The piston 18 and the closure member 24 can be made from conventional silicon rubber formulations. The other parts of the system 10 are preferably molded from a suitable plastic material for light weight and ease of fabrication. Suitable plastic materials for the system 10 include ABS, polycarbonate, and acetyl.

Although the present invention has been described in considerable detail with reference to certain preferred versions thereof, other versions are possible. For example, the ampule 14 can be made in other sizes for providing different medicament volumes. Also, the flange member 50 can be enlarged such that it is guided by the bore 28, and the boss portion 56 of the piston 18 can be formed as a rearward extension from the rear face 58 of the piston 18, particularly when the chamber diameter $C_D$ is very small. Therefore, the spirit and scope of the appended claims should not necessarily be limited to the description of the preferred versions contained herein.

What is claimed is:

1. A safety medicament injection system comprising:
   (a) an ampule comprising:
      (i) a housing forming at least a portion of a medicament chamber and having a front opening in fluid communication with the chamber;
      (ii) a resilient closure member for sealingly closing the front opening;
      (iii) resilient seal means for sealingly closing a rear portion of the chamber;
      (iv) a tubular tissue-piercing needle movably supported within the housing for axial movement from a cocked position to an extended position, the needle having a front outlet and an inlet rearwardly located relative to the outlet and in fluid communication therewith, the needle piercing the seal means and the closure member when moving from the cocked position to the extended position; and
      (v) needle biasing means for biasing the needle rearwardly from the extended position;
   (b) actuation means for advancing the needle from the cocked position to the extended position in response to external force, the chamber being compressed by the actuation means for feeding the medicament from the chamber, into the inlet and out of the outlet of the needle; and
   (c) the needle biasing means automatically moving the needle from the extended position to a final position in response to removal of the external force, the outlet of the needle being enclosed within the chamber in the final position for preventing accidental contact therewith following use of the system.

2. The system of claim 1, wherein the actuation means comprises a piston sealingly axially movable in the housing, the seal means being located on the piston.

3. The system of claim 2, further comprising a needle guide passage carried by the piston, the seal means including a pierceable end termination of the needle guide passage.

4. The system of claim 2, wherein the needle biasing means comprises a first helical compression spring coupled between the needle and the piston for urging the needle rearwardly relative to the piston.

5. The system of claim 4, comprising a flange member rigidly connected proximate a rear extremity of the needle for receiving a rear extremity of the first spring, the needle guide passage extending within a front extremity of the first spring.

6. The system of claim 5, wherein the flange member contacts the piston for limiting forward movement of the needle.

7. The system of claim 2, further comprising a pierceable cover member sealingly closing a rear portion of the housing, the piston and the needle being sealingly enclosed within the housing between the cover member and the closure member when the needle is in the cocked position, the cover member being pierced by application of the external force.

8. The system of claim 1, wherein the actuation means comprises means for coupling the inlet of the needle to the chamber between an intermediate position of the needle and the extended position, and means for feeding a major portion of the medicament from the outlet during movement of the needle between the intermediate position and the extended position.

9. The system of claim 8, wherein the needle is slidably supported on a piston, the piston being sealingly slidably supported by the housing for sizing the chamber, the seal means being located on the piston and proximate the needle outlet when the needle is in the cocked position.

10. The system of claim 9, wherein the actuation means comprises needle limit means for limiting forward movement of the needle relative to the piston between the intermediate position and the extended position, the piston being moved forwardly by the needle limit means during the feeding of the medicament.

11. The system of claim 1, further comprising an actuator unit for operating the ampule, the actuator unit comprising:
(a) a frame for releasably receiving the ampule;
(b) a plunger axially movable in the frame and having a handle portion extending rearwardly therefrom;
(c) a plunger spring connected between the frame and the plunger for rearwardly biasing the plunger, the needle being advanced from the cocked position to the extended position in response to a forwardly directed external force on the handle portion, the chamber being compressed by forward movement of the piston for feeding the medicament from the chamber, into the inlet and out of the outlet of the needle, the plunger retracting from the ampule when the external force is removed.

12. The system of claim 1, wherein the needle advances to an initial penetration depth of approximately 0.09 inch prior to delivery of medicament, the needle further advancing to a full penetration depth, the full penetration depth being approximately 0.39 inch greater than the initial penetration depth, up to approximately 0.5 cc of medicament being delivered from the needle during advancement of the needle between the initial and full penetration depths.

13. A safety medicament injection system comprising:
(a) an ampule comprising:
  (i) a housing forming at least a portion of a medicament chamber and having a front opening in fluid communication with the chamber;
  (ii) a resilient closure member for sealingly closing the front opening;
  (iii) a piston sealingly axially movable in the housing for sizing the chamber and having a needle guide passage formed integrally therewith, and a seal portion forming a pierceable end termination of the passage;
  (iv) a tubular tissue-piercing needle movably supported in the passage for movement from a cocked position to an extended position, the needle having a front outlet and an inlet rearwardly located relative to the outlet and in fluid communication therewith, and a flange member rigidly connected proximate a rear extremity of the needle, the needle piercing the seal portion of the piston and the closure member when moving from the cocked position to the extended position, the inlet of the needle being coupled to the chamber between an intermediate position of the needle and the extended position, the flange member contacting the piston for limiting forward movement of the needle, at least a major portion of the medicament being fed from the outlet during movement of the needle between the intermediate position and the extended position;
  (v) needle biasing means for biasing the needle rearwardly from the extended position, comprising a first helical compression needle spring coupled between the needle and the piston for urging the needle rearwardly relative to the piston, the flange member engaging a rear extremity of the needle spring, the needle guide passage extending within a front extremity of the needle spring; and
  (vi) a pierceable cover member sealingly closing a rear extremity of the housing, the piston and the needle being sealingly enclosed in the housing between the cover member and the closure member when the needle is in the cocked position;
(b) an actuator unit for operating the ampule, the actuator unit comprising:
  (i) a frame for releasably receiving the ampule;
  (ii) a plunger axially movable in the frame and having a handle portion extending rearwardly therefrom;
  (iii) a plunger spring connected between the frame and the plunger for rearwardly biasing the plunger, the cover member being pierced by the plunger and the needle being advanced from the cocked position the to extended position in response to a forwardly directed external force on the handle portion, the chamber being compressed by forward movement of the piston for feeding the medicament from the chamber, into the inlet and out of the outlet of the needle; and
(c) the needle being moved by the needle spring from the extended position to a final position in response to removal of the external force, the outlet of the needle being enclosed within the chamber in the final position for preventing accidental contact therewith following use of the system.

* * * * *